(12) United States Patent
Williams

(10) Patent No.: US 10,247,688 B2
(45) Date of Patent: Apr. 2, 2019

(54) MOISTURE DETECTING SYSTEM AND METHOD FOR USE IN AN IGBT OR A MOSFET

(71) Applicant: Kevin R. Williams, Cypress, TX (US)

(72) Inventor: Kevin R. Williams, Cypress, TX (US)

( * ) Notice: Subject to any disclaimer, the term of this patent is extended or adjusted under 35 U.S.C. 154(b) by 267 days.

(21) Appl. No.: 15/399,008

(22) Filed: Jan. 5, 2017

(65) Prior Publication Data

US 2018/0188197 A1    Jul. 5, 2018

(51) Int. Cl.
*G01N 27/04*    (2006.01)

(52) U.S. Cl.
CPC ......... *G01N 27/048* (2013.01); *G01N 27/045* (2013.01)

(58) Field of Classification Search
CPC ............................ G01N 27/048; G01N 27/045
USPC .................... 324/694, 693, 691, 649, 600
See application file for complete search history.

(56) References Cited

U.S. PATENT DOCUMENTS

| | | | |
|---|---|---|---|
| 4,272,986 A | 6/1981 | Lowry et al. | |
| 4,279,292 A | 7/1981 | Swiaposz | |
| 4,540,940 A * | 9/1985 | Nolan | G01R 19/145 324/133 |
| 4,788,626 A | 11/1988 | Neidig et al. | |
| 5,606,264 A | 2/1997 | Licari et al. | |
| 5,977,621 A | 11/1999 | Stuck | |
| 6,054,849 A * | 4/2000 | Collier | G01R 31/04 324/133 |
| 8,319,559 B2 * | 11/2012 | Kocer | H03F 1/3205 330/296 |
| 8,829,883 B2 * | 9/2014 | Samid | G05F 1/56 323/313 |
| 2002/0145435 A1 * | 10/2002 | Bald | G01R 31/2849 324/551 |
| 2004/0159146 A1 | 8/2004 | Belanger | |
| 2007/0029975 A1 * | 2/2007 | Martin | H02J 7/0068 320/134 |
| 2008/0094101 A1 * | 4/2008 | Balasubramanian | H03K 19/17732 326/38 |
| 2008/0212302 A1 | 9/2008 | Popp et al. | |
| 2009/0033298 A1 * | 2/2009 | Kleveland | G05F 1/575 323/271 |
| 2011/0115506 A1 | 5/2011 | Eriksson et al. | |
| 2013/0257177 A1 * | 10/2013 | Jacobson | H02M 1/08 307/115 |

FOREIGN PATENT DOCUMENTS

WO    WO 2016/070013 A1 *   5/2016

* cited by examiner

*Primary Examiner* — Giovanni Astacio-Oquendo
(74) *Attorney, Agent, or Firm* — Egbert Law Offices, PLLC

(57) ABSTRACT

A moisture detecting system has a power semiconductor module having a gate driver with the gate in which the gate driver has an on condition and an off condition, a power supply connected to the gate driver so as to supply voltage to the gate driver, a controller cooperative between the power supply and the gate driver so as to set the gate driver between the on condition and the off condition, and a sensor connected to the gate driver so as to detect a leakage of current across the gate driver. The controller is cooperative at the power supply so as to turn off the power supply when the signal is indicative of the leakage of current. The gate driver can an IGBT or a MOSFET.

5 Claims, 3 Drawing Sheets

MOISTURE DETECTING SYSTEM AND METHOD FOR USE IN AN IGBT OR A MOSFET

CROSS-REFERENCE TO RELATED APPLICATIONS

Not applicable.

STATEMENT REGARDING FEDERALLY SPONSORED RESEARCH OR DEVELOPMENT

Not applicable.

NAMES OF THE PARTIES TO A JOINT RESEARCH AGREEMENT

Not applicable.

INCORPORATION-BY-REFERENCE OF MATERIALS SUBMITTED ON A COMPACT DISC

Not applicable.

BACKGROUND OF THE INVENTION

1. Field of the Invention

The present invention relates to power semiconductors, such as IGBT's. More particularly, the present invention relates to the detection of moisture within the power semiconductors or modules.

2. Description of Related Art Including Information Disclosed Under 37 CFR 1.97 and 37 CFR 1.98

Power management subsystems control the distribution of power in an electronic system. The subsystems consist of integrated circuits and power semiconductors that handle power levels that can range from microwatts to megawatts. Power semiconductors employed in power management systems include power switches and rectifiers (diodes). Power switches include MOSFETs, IGBT's, and BJT (bipolar junction transistors). MOSFETs, IGDT's and BJT's are found in two different forms. First, they can be discreet power semiconductors in which the devices are only a single type housed in a single package, or they can be integrated power semiconductors which are integrated with other circuits in a single package so that they can be housed in a multi-chip module.

An IGBT is an insulated gate bipolar transistor which is a three-terminal power semiconductor noted for high-efficiency and modest switching speeds. It switches electrical power in many modern appliances: electric cars, variable speed refrigerators, and air conditioners. IGBT's are usually only discrete devices, or may have an integrated diode.

Power semiconductors, such as IGBT's, are widely used in power conversion equipment in many industries. While the environment for such equipment is generally well-controlled when the equipment is operating, prolonged periods of non-operation can result in the formation of condensation at different points within the equipment, including the internal connections of the power semiconductor modules. The condensation may be absorbed by the insulating gels used in the power semiconductor modules so as to make them at least partially conductive. Even if active condensation does not occur, in high humidity environments, the insulating gel material can directly absorb moisture from the atmosphere and become conductive. If main power is applied to the equipment in that condition, the power semiconductor module is likely to fail due to uncontrolled current flowing through the insulating gel.

An obvious solution to this problem is to use a commercial condensation detector to monitor conditions near to the power semiconductor module. Unfortunately, this method is generally not successful. The insulating gel in the power semiconductor module takes a significant amount of time (at least several hours) to both become dangerously compromised with moisture and to "dry out" when conditions improve. The power semiconductor module can become compromised due non-condensing humidity that is generally not detected by commercial condensation detection products.

Another widely-used solution to the problem is to pre-heat the system to ensure a complete dry-out prior to applying high-voltage. While this is successful in preventing system failure, it delays operation of the system for a prolonged period of time. This period of time can be typically twenty-four hours.

Moisture can impair the blocking ability of semiconductor chips incorporated in the module. The insulation strength can also be lost. With cut-off thyristors, the fine metallization paths or runs on the chips can corrode, which can cause interruptions in current or short circuiting between control and power electrodes.

No truly moisture-proof module constructions with a plastic housing are known. However, there have been various attempts to produce moisture-proof modules. In typical modules having a plastic housing and a ceramics substrate used as the bottom, leaks arise from the fact that the relatively thin plastic housing walls and the seams between the housing of the bottom plate allow water vapor to penetrate, because the adhesive is not perfect. The adhesive site may also tear open after frequent temperature changes. Such modules of this type are not durably moisture-proof even though the housing and substrate are both thin which permits elements to adapt to one another by flexing in response to temperature changes.

The moisture within these hermetic packages can cause premature device failure to due to electrogalvanic corrosion of chip metallization. The ability to know the amount of moisture in the package thus becomes a critical parameter both for operating reliability as well as process technology improvements and quality control.

An in-situ monitor, in which a sensing device is mounted directly in a package, or incorporated into the design of a circuit, offers rapid availability of moisture data. The analysis cost per sample is inexpensive. This means that statistically significant numbers of packages can be analyzed on a more frequent basis. The in-situ monitor thus enables more exacting process development experimentation and process control measurements, and speeds up vendor and assembly lot qualifications. Moreover, the in-cavity sensor gives a real-time dynamic analysis of moisture within a package. The determination can be made repeatedly so that moisture conditions can be monitored as a function of part storage or operating lifetime.

Two classes of in-situ sensors for integrated circuit packages have been developed. The first is the a surface conductivity sensor and the second is a volume effect sensor. The surface conductivity sensor measures the conductivity of moisture condensed on non-porous surfaces between two spaced electrodes using a "dew point test". The volume effect sensor measures the conductivity of a porous surface which absorbs moisture.

In the past, various patents have issued relating to power semiconductors and moisture detection. For example, U.S. Pat. No. 4,272,986, issued on Jun. 16, 1981 to Lowry et al., shows a means and method for measuring moisture content of hermetic semiconductor devices. In particular, this method includes a pattern of interdigitated thin film aluminum conductors provided on an impurity-free, non-porous silicon oxide insulative substrate. The surface conductivity of this structure rises as moisture condenses onto and between the conductors as the temperature is reduced at a slow-controlled rate to the dew point temperature. The amplitude of the maximum surface conductivity is proportional to ionic impurity concentration.

U.S. Pat. No. 4,279,292, issued on Jul. 21, 1981 to E. Swiaposz, describes a temperature and moisture regulator for integrated circuits. This temperature and moisture regulator comprises an insulated mount for the device whose temperature and moisture is to be regulated, a first thermoelectric cooler is in effective contact with both a certain substantial central area of the device and one end of an elongated metal heat-sink. A plurality of resilient heat-conductive, thermal-feedback fingers are metallurgically bonded at one of the ends thereof to the heat sink and are urged against a portion of the surface area of the device at the other ends thereof in predetermined spatial dispositions from but in proximity with the central area that is in contact with the thermoelectric cooler. Both cooled and heated areas occur on various surfaces of the device. A second thermoelectric cooler is effectively connected between the other end of the heat sink and a heat exchanger.

U.S. Pat. No. 4,788,626, issued on the Nov. 29, 1988 to Neidig et al., teaches a power semiconductor module that includes a plastic housing having an interior. A substrate in the form of a ceramic plate with upper and lower surfaces is inserted in the housing as a housing bottom. Metallizations are disposed on the upper and lower surfaces of the ceramic plate. The metallization on the upper surface of the ceramic plate faces the interior of the housing and a structure forms conductor paths. Semiconductor components, connecting elements and terminal elements for external terminals are all disposed on the upper surface of the ceramic plate. A frame is connected to the substrate in the interior of the housing for sealing against moisture.

U.S. Pat. No. 5,606,264, issued on Feb. 25, 1997 to Licari et al., describes a moisture sensor for electronic modules. This moisture sensor is a separate chip which is packaged in the same module with a circuit to be checked and having pin-outs that can be tested with a circuit that is usually external. The sensor makes use of the moisture-induced migratory behavior that causes the problem by using a highly migratory metal or alloy to define paired electrodes. The metal of the electrodes undergoes rapid ionization and migration in the presence of trace amounts of moisture, dissolved ionic contaminants, and a small potential difference across the electrodes. The moisture which actuates the sensor, triggers the circuit long before the level of seepage and electromigratic represents a present danger of circuit failure.

U.S. Pat. No. 5,977,621, issued on Nov. 2, 1999 to A. Stuck, shows a power semiconductor module in which a layer of foam is arranged under the housing cover in the housing. The foam not only enables mechanical support of the potting compound so that the potting compound is prevented from becoming detached, but can also absorb a large pressure increase in the event of a short-circuit by virtue of compression.

U.S. Patent Application Publication No. 2004/0159146, published on Aug. 19, 2004 to M. Belanger, shows a method and device for monitoring the moisture content level of a solid dielectric material immersed in a dielectric fluid. The device includes a moisture detector and a temperature detector for measuring the oil moisture content and temperature levels, respectively. A microprocessor is electrically connected to both the moisture and temperatures detectors. The microprocessor known water solubility properties of the paper and the oil stored therein acting along with the oil/gas content level and the enclosure pressure related data. The microprocessor processes the oil moisture content level and the oil temperature level so as to determine the paper moisture content level and the bubble temperature.

U.S. Patent Application Publication No. 2008/0212302, published on Sep. 4, 2008 to Popp et al., describes a housing for a power semiconductor module. The power semiconductor module has the load-connecting elements arranged thereon. The contact devices are arranged in housing troughs on the exterior of the housing. The housing is closed by a cover. The housing is preferably formed as a unitary piece of material having a circumferential sealing frame and the cover includes an outer rim that extends over the circumferential sealing frame to prevent the penetration of fluid or moisture into the power semiconductor module when the cover is closed.

U.S. Patent Application Publication No. 2011/0115506, published in May 19, 2011 to Eriksson et al., provides a test body for use in determining moisture content in a laminated insulation of a power transformer by measuring a dielectric frequency response of the test body. The test body has a laminated structure of the same material as the laminated insulation and has a shape and a size to obtain my moisture content characteristics to resemble the moisture content characteristics of the laminated power transformer insulation.

It is an object of the present to provide a system and method that serve to protect power semiconductors from moisture and condensation.

It is another object of the present invention to provide a system and method that avoids premature power semiconductor module failure.

It is still a further object the present invention provide a system and method that effectively determines the existence of moisture affecting the power semiconductors.

It is another object of the present invention to provide a system and method that determines the existence of moisture so as to avoid the application of power to the power semiconductor module under conditions in which moisture exists.

These and other objects and advantages of the present invention will become apparent from a reading of the attached specification and appended claims.

BRIEF SUMMARY OF THE INVENTION

The present invention is a moisture detecting system that comprises a power semiconductor module having a gate driver with a gate in which the gate driver has an on condition and an off condition, a power supply connected to the gate driver so as to supply voltage to the gate driver, a controller cooperative between the power supply and the gate driver in which the controller sets the gate driver between the on condition and the off condition, and a sensor connected to the gate driver so as to detect a leakage of current across the gate driver.

In one embodiment of the present invention, the sensor comprises a resistor connected in series with the gate driver. An amplifier is connected to the resister so as to measure and amplify voltage across the resistor. The controller is connected to the amplifier so as to receive the measured amplified voltage. The controller sends a signal indicative of the leakage of current across the gate driver. The controller is cooperative with the power supply so as to turn off the power supply when the signal is indicative of the leakage of current.

In another embodiment of the present invention, the controller is connected the gate of the gate driver so as to directly measure gate voltage. The controller maintains the off condition for a period of time. The controller monitors when the measured gate voltage decays beyond a desired rate. A transistor is connected in series with the gate of the gate driver so as to hold the gate voltage. An amplifier is connected between the controller and the gate driver so as to measure and amplify the measured gate voltage during the period of time. The controller is cooperative with the power supply so as to turn off the power supply when the measured gate voltage decays beyond the desired rate.

In the present invention, the gate driver can be either an IGBT or a MOSFET.

The present invention is also a moisture detecting circuit for use with a gate driver of a power semiconductor module. The moisture detecting circuit includes a power supply adapted to be connected to the gate driver, a controller cooperative between the power supply and the gate driver so as to set the gate driver between a on-condition and off condition, and a sensor adapted to be connected to the gate of the gate driver so as to detect a leakage of voltage across the gate driver. In one embodiment, the sensor includes a receiver connected in series with the gate driver. An amplifier is connected to the resistor so as to measure and amplify voltage across the resistor. The controller is connected to the amplifier so as to receive the measured and amplified voltage and then to send a signal indicative of the leakage of current across the gate driver. The controller is cooperative with the power supply so as to turn off the power supply when the signal is indicative of the leakage of current. Alternatively, the moisture detecting circuit can include a controller connected to the gate of gate driver so as to directly measure gate voltage. The controller maintains the off condition for a period of time. The controller monitors the measure gate when the measured gate voltage decays beyond a desired rate. A transistor is connected in series with the gate of the gate driver so as to hold the gate voltage. The controller is cooperative at the power supply so as to turn off the power supply when the measured gate voltage the case is beyond the desired rate.

The present invention is also a method of measuring moisture in a power semiconductor module. This method includes the steps of: (1) applying a control voltage to the gate driver; (2) switching the gate driver to an off condition for a period of time; (3) sensing a leakage of the voltage across the gate driver for a period of time; and (4) sending a control signal to remove voltage from the gate driver if a decay of voltage across the gate driver during the period of time is beyond the desired rate. The sensed leakage of voltage across the gate driver is amplified. The gate driver is isolated from a main power supply prior to the step of applying the control voltage.

This foregoing Section is intended to describe, with particularity, the preferred embodiments of the present invention. It is understood that modifications to these preferred embodiments can be made within the scope of the present invention. As such, this Section should not to be construed, in any way, as limiting of the broad scope of the present invention. The present invention should only be limited by the following claims and their legal equivalents.

DETAILED DESCRIPTION OF THE INVENTION

Figure 1:
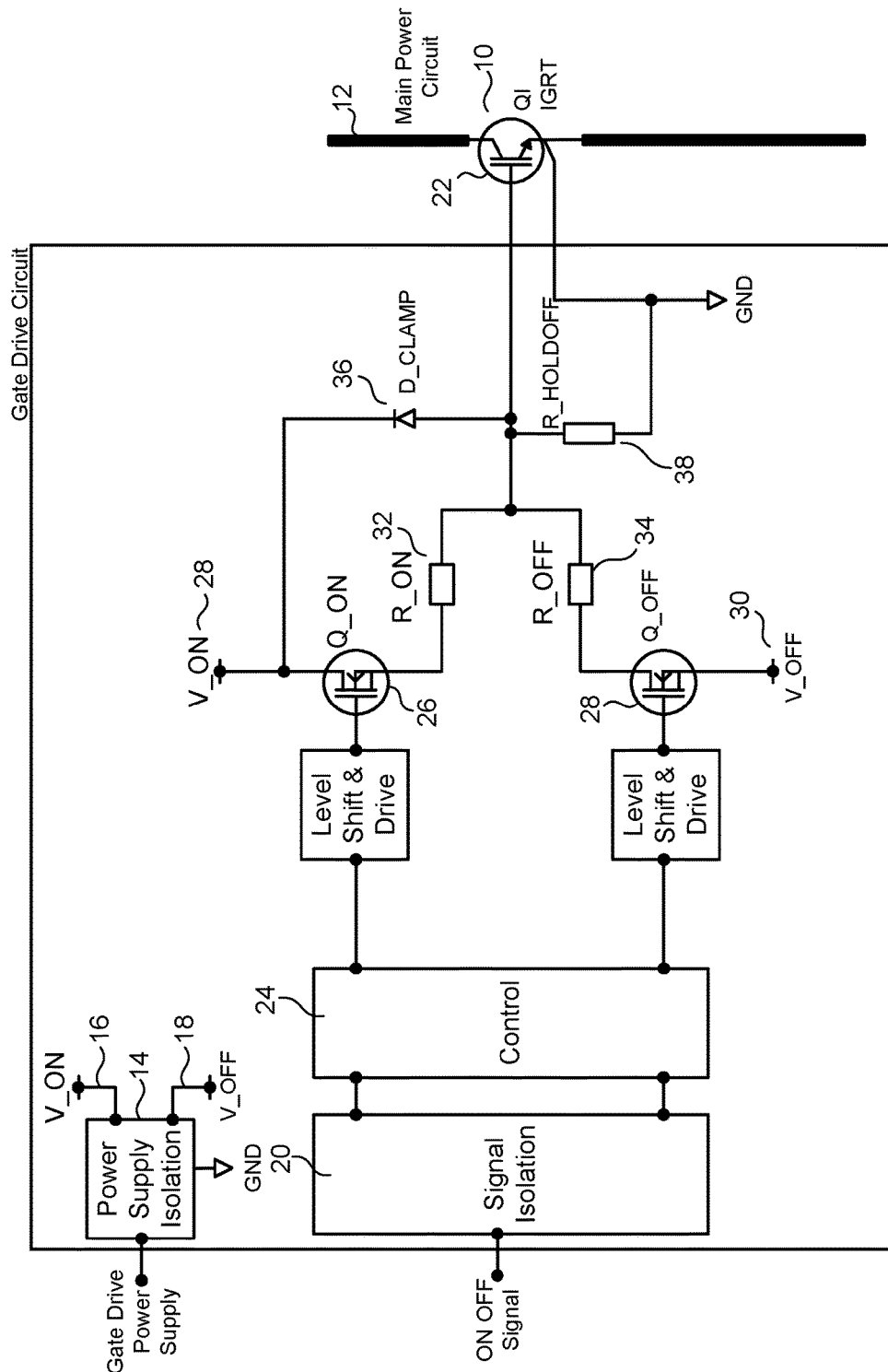
FIG. 1 is a schematic illustration of a prior art gate drive for a power semiconductor module.

FIG. 1 shows a typical gate drive for a power semiconductor module. In particular, the power semiconductor module 10 is either an IGBT or a MOSFET that is connected to a main power circuit 12. The power semiconductor module 10 has gates extending connected to the main power circuit. A power supply isolation circuit 14 provides high voltage isolation between the external electronics power supply and the gate driver of the power semiconductor module 10. The power supply isolation 14 also provides the regulated supply voltage V_ON 16 and V_OFF 18 that are used to drive the gate voltage of the IGBT 10. The signal isolation 20 provides the high-voltage isolation between the external control electronics and the gate drive. In its simplest form, the signal isolation 20 allows a single on/off command to be sent to the gate drive 22. The controller 24 is an electronic circuit that is used to control the status of the Q_ON transistor 26 and the Q_OFF transistor 28. Typical control is implemented using low-voltage logic circuits and analog interfaces. The V_ON 28 is a positive voltage (typically 15 V) that is used to turn on the gate driver 22. Voltage V_OFF 30 is a negative voltage (typically between −8 and −15 V) that is used to turn the gate driver 22 off. The Q_ON transistor 26 and the Q_OFF transistor 28 are the transistors that switch the gate voltage of the gate driver 22 between the V_ON and V_OFF levels. These transistors 26 and 28 are typically medium power MOSFET devices. The R_ON resistor 32 and the R_OFF resistor 34 are resistors that are used to set the charging and discharging current of the gate of the gate driver 22. The D_CLAMP diode 36 is a diode used to clamp the gate voltage of the gate driver 22 to a maximum of V_ON under certain operating conditions. The R HOLD OFF resistor 38 is used to hold the gate voltage of the gate driver 22 to approximately zero when the gate drive circuit is not powered.

Figure 2:
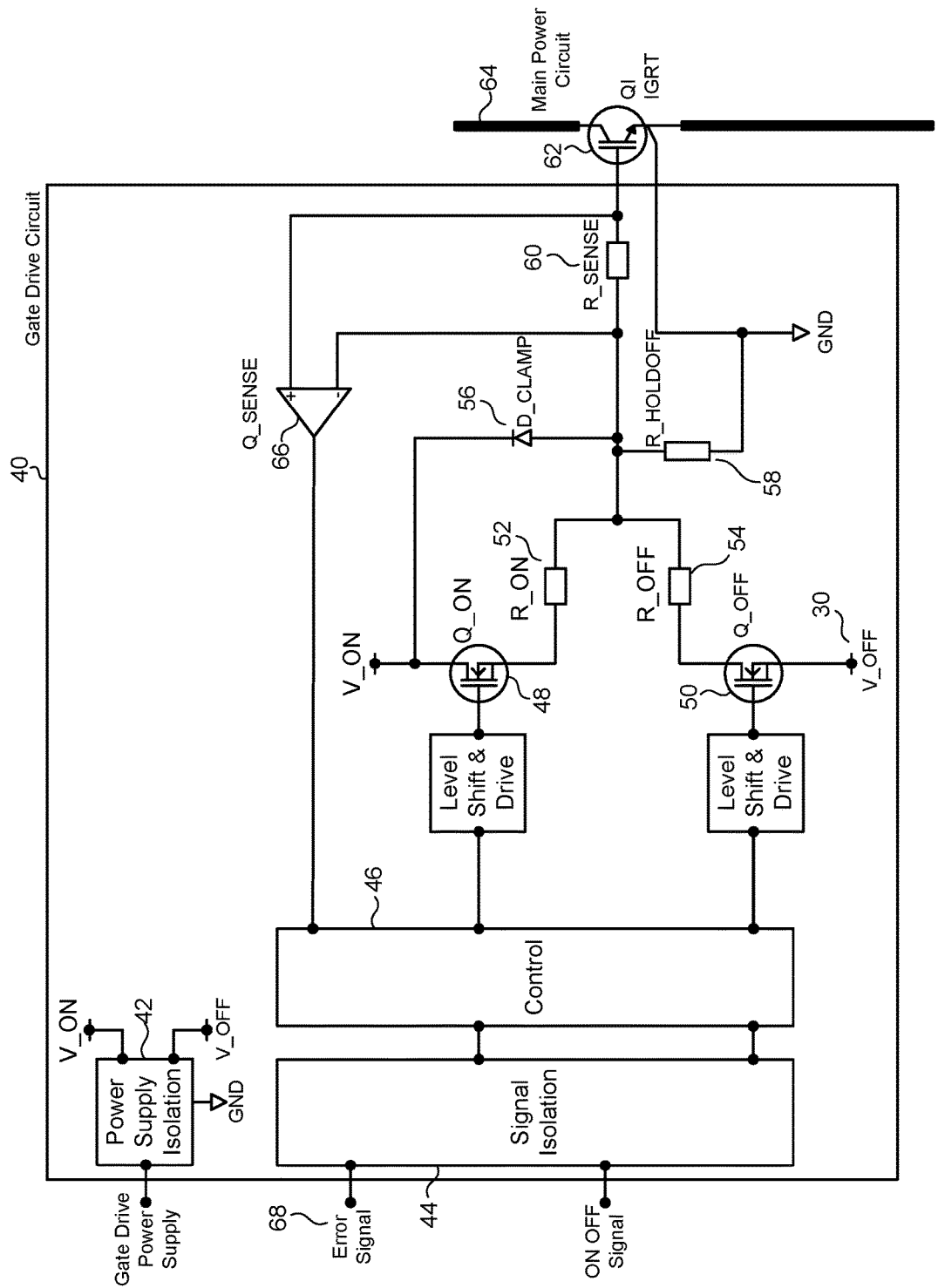
FIG. 2 is a schematic illustration of a first embodiment of the moisture detecting system of the present invention.

FIG. 2 shows the moisture detecting circuit 40 in accordance with one embodiment of the present invention. In relation to FIG. 1, the moisture detecting circuit 40 will include the power supply isolation circuit 42, the signal isolation 44 of the controller 46, transistors 48 and 50, resistors 52 and 54, clamp 56 and resistor 58. In this embodiment, the standard circuit of FIG. 1 is modified by adding a current sensing resistor 60 in the gate connection of the gate driver 62. Gate driver 62 is connected to a main power circuit 64. The gate driver 62 can be an IGBT or a MOSFET.

The voltage across the resistor 60 is monitored by amplifier 66. When the controller 46 identifies that the gate driver 62 is in a steady-state off condition, it detects excess leakage current in the current sensing resistor 60 to maintain the desired gate charging current. In particular, when amplifier 66 detects excess leakage current, it will send an error signal 68 to the controller 46. This error signal 68 can be connected to an indicator or a monitor so that the leakage of current across the gate driver 22 is noticed. It can also send a signal to the power supply 42 so as to stop the control voltage flowing to the gate driver 62. Also, the controller 46 can switch the main power circuit 64 to an off condition so that current no longer flows to the gate driver 62.

The moisture detecting circuit 40 allows for the measurement of moisture and the detection of gate leakage current in an insulated gate device such as an IGBT or a MOSFET. In particular, the gate leakage current is measured when the gate device is in a steady-state "off" condition. Under normal safe conditions, this value is very small (typically less than 1 µA). Under those circumstances where moisture is absorbed into the insulating gel of the gate device, additional leakage current flows through the compromise gel. This additional current is detected by the moisture detecting circuit 40. In particular, the moisture detecting circuit 40 provides for direct measurement of current by monitoring the voltage drop across the resistor 60 in the steady-state off condition. This will require very precise analog circuits since the voltage drop will be very small. Ultimately, in the present invention, the gate driver 62 signals this dangerous condition to a larger system control so that the application of main power through the main power circuit 64 is prevented. This requires a system where the control power (including the gate driver circuit power) is available before the main power is applied.

Figure 3:
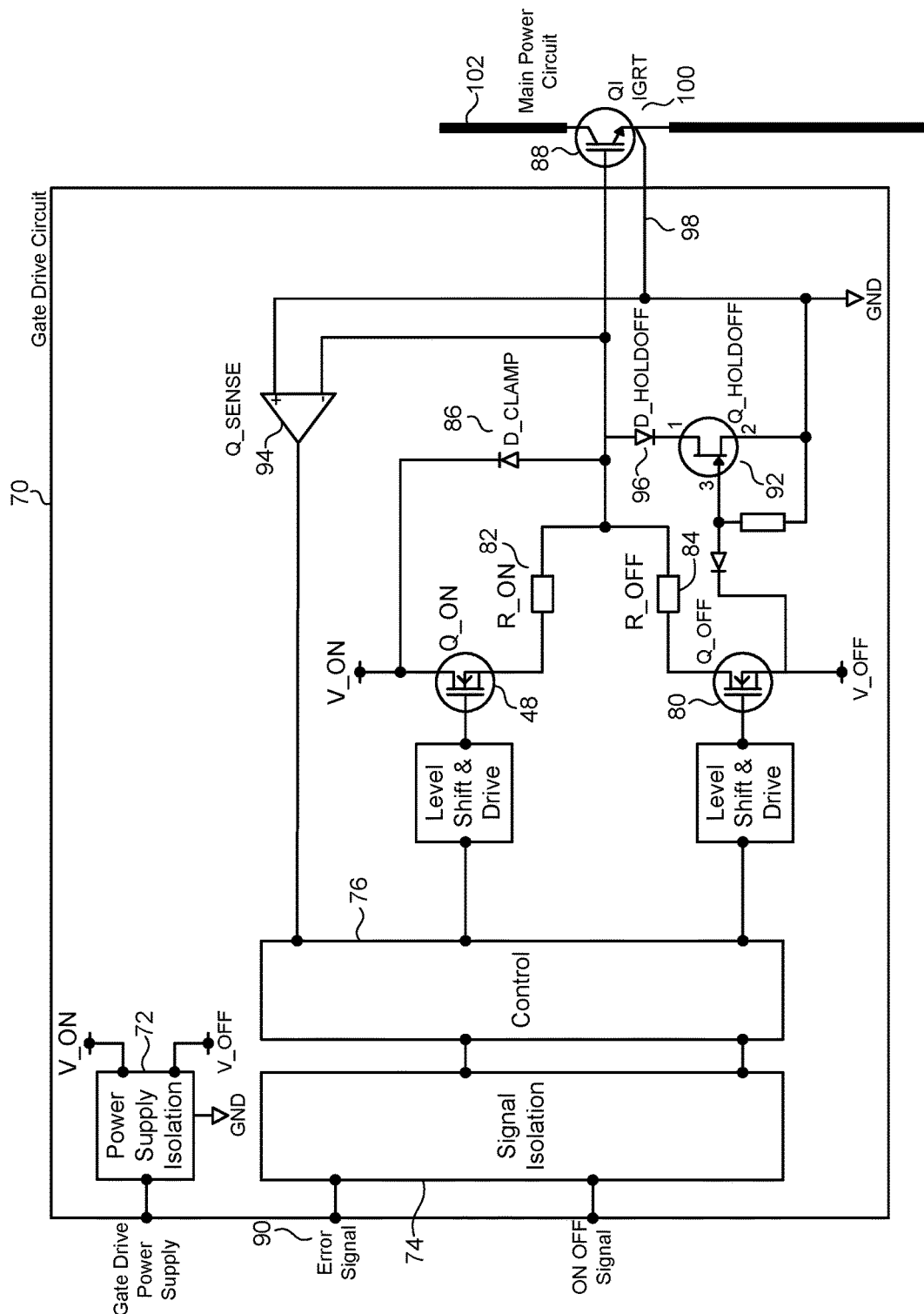
FIG. 3 is a schematic illustration of a second embodiment of the moisture detecting system of the present invention.

FIG. 3 shows an another embodiment of the moisture detecting circuit 70 of the present invention. The moisture detecting circuit 70 is similar to the gate driver circuit shown in FIG. 1 except for the additional several items in order to measure the leakage of current. In particular, the moisture detecting circuit 70 will include the power supply isolation 72, the signal isolation 74, the controller 76, the transistors 78 and 80, the resistors 82 and 84, and the diode 86. In contrast of FIG. 2, the moisture detecting circuit 70 is modified by directly measuring and monitoring the gate voltage of the gate driver 88 by the controller circuit 76. When the system is in a steady-state off condition, the controller 76 will momentarily current off both the transistors 78 and 80. When in this state, the gate voltage should remain at the V_OFF potential for a period of time due to the gate input capacitance. This period of time can be approximately hundreds of milliseconds. If the gate voltage on the gate driver 88 is seen to fall to rapidly, this is an indication of excess leakage current and an error signal 90 is signaled. In contrast to the previous embodiment, the previous resistor 58 is replaced with the active circuit around the Q_HOLD-OFF transistor 92 since the current in the resistor 58 of the previous embodiment would make detection of gate leakage current impossible. An amplifier 94 serves to amplify the signal from the gate driver 88 prior to passing to the controller 76. The D_HOLDOFF diode 96 is connected to the transistor 92 and in series with the gate driver 88 so as to stop against clamping at negative voltages. Line 98 is connected to the amplifier 94 and extends to a gate 100 of the gate driver 88. As such, the controller 76 is able to measure directly the voltage at the gate 100 of the gate driver 88. Fundamentally, if there is no moisture in the gate driver 88 or the power semiconductor module, then there would be no loss of voltage across the gates of the gate driver 88. In contrast, if there is a decay of voltage in the gate driver 88, this would be detected. If the decay is beyond an acceptable rate, then this is indicative of moisture content and, as such, the controller 76 will send the error signal so as to isolate the gate driver 88 from the control power supply 72 and from the main power supply running along main power circuit 102. As such, the moisture detecting circuit 70 of FIG. 3 measures the rate of change of gate voltage when the gate driver 88 is momentarily switched into a high impedance condition.

Fundamentally, the moisture detecting system of the present invention allows the operator to determine if condensation or module is affecting the power semi conductor module. It has been noted that problems with power semiconductor modules is that the condensation or moisture can cause module failures. As such, the present invention allows for detecting of moisture so as to avoid module failures. If moisture is detected prior to the application of power to the power semiconductor module, then this can provide an immediate indication of the need to avoid the application of power. Since the detecting the moisture can be done relatively rapidly, the present invention is able to avoid long periods of downtime for the power semiconductor module. Once no moisture is detected, then the power can be provided to the power semiconductor module. Typically in the past, as a preventive measure, the power semiconductor module is shut down for a period of time or placed into a high temperature conditions so as to dry out the module. The present invention avoids the need for the downtime or for the drying out process.

The foregoing disclosure and description of the invention is illustrative and explanatory thereof. Various changes in the details of the illustrated construction or in the steps of the described method can be made within the scope of the present claims without departing from the true spirit of the invention. The present invention should only be limited by the following claims and their legal equivalents.

I claim:

1. A moisture detecting system comprising:
    a power semiconductor module having a gate driver that has a gate, said gate having an on condition and an off condition;
    a power supply connected to said gate driver so as to supply voltage to said gate drive:
    a controller cooperative between said power supply and said gate drive: said controller setting said gate driver between the on condition and the off condition; and
    a sensor connected to said gate so as to detect a leakage of current across said gate driver, said sensor comprising a resistor connected in series with said gate; and
    an amplifier connected to said resistor so as to measure and amplify voltage across said resistor, said controller connected to said amplifier so as to receive the measured and amplified voltage, said controller sending a signal indicative of the leakage of current across said gate drive, said controller cooperative with said power supply so as to turn off said power supply when the signal is indicative of the leakage of current as a result of moisture in said power semiconductor module.

2. The moisture detecting system of claim 1, said gate driver selected from the group consisting of an IGBT and a MOSFET.

3. A moisture detecting system comprising:
    a power semiconductor module having a gate driver that has a gate, said gate having an on condition and an off condition;
    a power supply connected to said gate driver so as to supply voltage to said gate drive:

a controller cooperative between said power supply and said gate drive, said controller setting said gate driver between the on condition and the off condition; and a sensor connected to said gate so as to detect a leakage of current across said gate driver, said controller connected to said gate of said gate driver so as to directly measure gate voltage, said controller for maintaining the off condition for a period of time, said controller monitoring when the measured gate voltage decays beyond a desired rate;

a transistor connected in series with said gate at said gate driver so as to hold the gate voltage; and an amplifier connected between said controller and said gate driver so as to measure and amplify the measured gate voltage during the period of time, said controller cooperative with said power supply so as to turn off said power supply when the measured gate voltage decays beyond the desired rate as a result of moisture in said power semiconductor module.

4. A moisture detecting circuit for use with a gate driver of a power semiconductor module, the moisture detecting circuit comprising:

a power supply adapted to be connected to the gate driver:

a controller cooperative between the power supply and the gate driver said controller setting the gate driver between and on condition and an off condition;

a sensor adapted to be connected to a gate of the gate driver so as to detect a leakage of voltage across the gate drive, said sensor being a resistor connected in series with the gate driver;

an amplifier connected to said resistor so as to measure and amplify voltage across said resistor, said controller connected to said amplifier so as to receive the measured and amplified voltage, said controller sending a signal indicative of the leakage of current across the gate driver, as a result of moisture in said power semiconductor module.

5. The monster detecting system of claim 4, said controller cooperative with said power supply so as to turn off said power supply when the signal is indicative of the leakage of current.

* * * * *

UNITED STATES PATENT AND TRADEMARK OFFICE
CERTIFICATE OF CORRECTION

Page 1 of 1

PATENT NO. : 10,247,688 B2
APPLICATION NO. : 15/399008
DATED : April 2, 2019
INVENTOR(S) : Williams et al.

It is certified that error appears in the above-identified patent and that said Letters Patent is hereby corrected as shown below:

On the Title Page

Item (12) should read:
Williams et al.

Item (72) should read:
Kevin R. Williams, Cypress, TX (US);
Gary Pace, Leander, TX (US)

Signed and Sealed this
Eleventh Day of January, 2022

Drew Hirshfeld
*Performing the Functions and Duties of the*
*Under Secretary of Commerce for Intellectual Property and*
*Director of the United States Patent and Trademark Office*